US009778265B2

(12) United States Patent
Anderson et al.

(10) Patent No.: US 9,778,265 B2
(45) Date of Patent: Oct. 3, 2017

(54) CHARGED PEPTIDE APPENDAGE TO FACILITATE ORIENTED PROTEIN COVALENT IMMOBILIZATION

(71) Applicants: George P. Anderson, Bowie, MD (US); Jinny Lin Liu, Ellicott City, MD (US); Marc P. Raphael, Springfield, VA (US); Ellen R. Goldman, Germantown, MD (US)

(72) Inventors: George P. Anderson, Bowie, MD (US); Jinny Lin Liu, Ellicott City, MD (US); Marc P. Raphael, Springfield, VA (US); Ellen R. Goldman, Germantown, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 104 days.

(21) Appl. No.: 14/688,010

(22) Filed: Apr. 16, 2015

(65) Prior Publication Data

US 2016/0305948 A1   Oct. 20, 2016

(51) Int. Cl.
| | |
|---|---|
| *G01N 33/68* | (2006.01) |
| *C07K 14/00* | (2006.01) |
| *C12N 15/62* | (2006.01) |
| *G01N 33/531* | (2006.01) |
| *G01N 33/543* | (2006.01) |
| *C07K 19/00* | (2006.01) |
| *C07K 16/16* | (2006.01) |

(52) U.S. Cl.
CPC .............. *G01N 33/68* (2013.01); *C07K 14/00* (2013.01); *C07K 19/00* (2013.01); *C12N 15/62* (2013.01); *G01N 33/531* (2013.01); *G01N 33/54393* (2013.01); *C07K 16/16* (2013.01); *C07K 2317/569* (2013.01); *C07K 2319/73* (2013.01); *G01N 2333/42* (2013.01)

(58) Field of Classification Search
CPC ................ C07K 16/00; C07K 2319/00; C07K 2317/569; C07K 2317/73; C07K 16/16
See application file for complete search history.

(56) References Cited

U.S. PATENT DOCUMENTS

| | | |
|---|---|---|
| 5,800,988 A | 9/1998 | Casterman et al. |
| 5,840,526 A | 11/1998 | Casterman et al. |
| 5,874,541 A | 2/1999 | Casterman et al. |
| 6,005,079 A | 12/1999 | Casterman et al. |
| 6,015,695 A | 1/2000 | Casterman et al. |
| 6,765,087 B1 | 7/2004 | Casterman et al. |
| 7,700,334 B2 | 4/2010 | Camarero et al. |
| 7,888,134 B2 | 2/2011 | Zeng et al. |
| 2006/0057637 A1* | 3/2006 | Anderson .............. B82Y 15/00 435/7.1 |
| 2011/0177615 A1 | 7/2011 | Hopkins |
| 2011/0301057 A1 | 12/2011 | Propheter et al. |
| 2012/0238039 A1 | 9/2012 | Cha et al. |

FOREIGN PATENT DOCUMENTS

EP   2124057 A1   11/2009

OTHER PUBLICATIONS

Chen et al. (Adv Drug Deliv Rev. Oct. 15, 2013; 65(10): 1357-1369).*
Goldman et al. (Proc. of SPIE 2013; vol. 8723 872313-9).*
Mooney et al (J Immunol Sep. 15, 2004, 173 (6) 3953-3961.*
PET22b Vector manual (1998, retrieved from http://www.helmholtz-muenchen.de/fileadmin/PEPF/pET_vectors/pET-22b_map.pdf on Jan. 22, 2017).*
Trilling et al. "Orientation of llama antibodies strongly increases sensitivity of biosensors" Biosensors and Bioelectronics 2014, 60: 130-136.

* cited by examiner

*Primary Examiner* — Tracy Vivlemore
*Assistant Examiner* — Carmencita M Belei
(74) *Attorney, Agent, or Firm* — US Naval Research Laboratory; Roy Roberts (57) ABSTRACT

Genetic fusions of proteins, for example single-domain antibodies (sdAbs), with a positively-charged domain enhanced immobilization of active protein in a desired orientation.

1 Claim, 6 Drawing Sheets

FIG. 1

Ricin Assay (Bt-D1 : NA-rPE (3:1))

SEQUENCE LISTING

```
<160> NUMBER OF SEQ ID NOS: 5

<210> SEQ ID NO 1
<211> LENGTH: 51
<212> TYPE: PRT
<213> ORGANISM: Artificial Sequence
<220> FEATURE:
<223> OTHER INFORMATION: synthetic construct

<400> SEQUENCE: 1

Ala Ala Ala Gly Gly Gly Gly Ser Gly Gly Gly Gly Ser Gly Gly Gly
1               5                   10                  15

Gly Ser Ala Gln Leu Lys Lys Leu Gln Ala Leu Lys Lys Lys Asn
            20                  25                  30

Ala Gln Leu Lys Trp Lys Leu Gln Ala Leu Lys Lys Lys Leu Ala Gln
        35                  40                  45

Gly Gly Asp
    50

<210> SEQ ID NO 2
<211> LENGTH: 16
<212> TYPE: PRT
<213> ORGANISM: Artificial Sequence
<220> FEATURE:
<223> OTHER INFORMATION: synthetic construct

<400> SEQUENCE: 2

Ala Ala Ala Gly Gly Gly Gly Ser Gly Gly Gly Gly Ser Lys Lys Lys
1               5                   10                  15
```

```
<210> SEQ ID NO 3
<211> LENGTH: 186
<212> TYPE: PRT
<213> ORGANISM: Artificial Sequence
<220> FEATURE:
<223> OTHER INFORMATION: synthetic construct

<400> SEQUENCE: 3
```

Glu Val Gln Leu Gln Ala Ser Gly Gly Gly Leu Val Gln Gly Gly Asp
1               5                   10                  15

Ser Leu Arg Leu Ser Cys Ala Ala Ser Gly Arg Thr Leu Gly Asp Tyr
            20                  25                  30

Gly Val Ala Trp Phe Arg Gln Ala Pro Gly Lys Glu Arg Glu Phe Val
        35                  40                  45

Ser Val Ile Ser Arg Ser Thr Ile Ile Thr Asp Tyr Ala Asn Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Val Tyr Tyr Cys
                85                  90                  95

Ala Val Ile Ala Asn Pro Val Tyr Ala Thr Ser Arg Asn Ser Asp Asp
            100                 105                 110

Tyr Gly His Trp Gly Gln Gly Thr Gln Val Thr Val Ser Ser Ala Ala
        115                 120                 125

Ala Gly Gly Gly Ser Gly Gly Gly Ser Gly Gly Gly Ser
    130                 135                 140

Ala Gln Leu Lys Lys Lys Leu Gln Ala Leu Lys Lys Lys Asn Ala Gln
145                 150                 155                 160

Leu Lys Trp Lys Leu Gln Ala Leu Lys Lys Lys Leu Ala Gln Gly Gly
                165                 170                 175

Asp Ala Leu Glu His His His His His His
            180                 185

```
<210> SEQ ID NO 4
<211> LENGTH: 167
<212> TYPE: PRT
<213> ORGANISM: Artificial Sequence
<220> FEATURE:
<223> OTHER INFORMATION: synthetic construct

<400> SEQUENCE: 4
```

Glu Val Gln Leu Gln Ala Ser Gly Gly Gly Leu Val Gln Gly Gly Asp
1               5                   10                  15

Ser Leu Arg Leu Ser Cys Ala Ala Ser Gly Arg Thr Leu Gly Asp Tyr
            20                  25                  30

Gly Val Ala Trp Phe Arg Gln Ala Pro Gly Lys Glu Arg Glu Phe Val
        35                  40                  45

Ser Val Ile Ser Arg Ser Thr Ile Ile Thr Asp Tyr Ala Asn Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Val Tyr Tyr Cys
                85                  90                  95

Ala Val Ile Ala Asn Pro Val Tyr Ala Thr Ser Arg Asn Ser Asp Asp
            100                 105                 110

Tyr Gly His Trp Gly Gln Gly Thr Gln Val Thr Val Ser Ser Glu Pro
        115                 120                 125

-continued

```
Lys Thr Pro Lys Pro Gln Pro Ala Ala Ser Gly Ala Glu Phe Ala Ala
    130             135                 140

Ala Gly Gly Gly Gly Ser Gly Gly Gly Ser Lys Lys Lys Ala Leu
145             150                 155                 160

Glu His His His His His His
                165

<210> SEQ ID NO 5
<211> LENGTH: 9
<212> TYPE: PRT
<213> ORGANISM: Artificial Sequence
<220> FEATURE:
<223> OTHER INFORMATION: synthetic construct

<400> SEQUENCE: 5

Ala Leu Glu His His His His His His
1               5
```

CHARGED PEPTIDE APPENDAGE TO FACILITATE ORIENTED PROTEIN COVALENT IMMOBILIZATION

BACKGROUND

Many immunoassays rely on monoclonal or polyclonal antibodies (IgG) derived from mice, rabbits, goats, or sheep as recognition elements. Considerable work has demonstrated that oriented capture molecules retain more binding ability and improve the performance of the assay. However natural proteins have limited means by which they can be oriented.

With advent of molecular biology, recombinant proteins including antibody fragments are being produced and utilized in increasing numbers. These recombinant proteins can be optimized for any number of parameters including oriented immobilization, as seen in, for example, U.S. Pat. No. 7,888,134, relating to electrostatic adsorption of scFv to a negatively charged surface.

In many respects it can be even more critical to orient small recombinant antibody derivatives because they have been reduced to only the active domain, thus reducing the number of random attachment sites that will not impair function. The same is likely true of many recombinant enzymes as well.

While there have been specialized methods developed for particular surfaces or using non-natural amino acids, the vast majority of covalent protein surface immobilization as well as dye/biotin molecule attachment chemistry makes use of either a carbodiimide or succinimide ester chemistry, which links a carboxyl group on one molecule to an amine on another. The limitation for successful orientation of proteins with these chemistries is that proteins possess a number of carboxyl and amine residues spread across their surface. The challenge has been to successfully orient the protein or attach the dye/biotin in a particular location so as to preserve maximal activity of the protein.

A need exists for a facile and effective technique to control the orientation of peptides and proteins, particularly antibodies, upon their immobilization.

BRIEF SUMMARY

In a first embodiment, a fusion protein includes a polypeptide, and a positively-charged domain with at least 85% sequence identity to SEQ ID No: 1 or SEQ ID No: 2 fused to the N-terminus or C-terminus of the polypeptide.

In a second embodiment, the polypeptide of the first embodiment is a single-domain antibody and the fusion is at the C-terminus thereof.

In a further embodiment, a method of attaching a fusion protein includes allowing a fusion protein according to the first or second embodiment to attach to a surface.

An additional embodiment is a method of analysis, including providing a surface having an antibody of the second embodiment attached thereto, contacting the surface with an analyte, and assaying the surface to determine whether an antigen of the antibody is present in the analyte.

BRIEF DESCRIPTION OF THE DRAWINGS

FIGS. 6A through 6C show results from localized surface plasmon resonance spectroscopy and imaging (LSPRi) tests.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

The reactions and purification techniques involved in performing this invention are conducted according to manufacturer's specifications or as commonly accomplished in the art or as described herein. The foregoing techniques and procedures are generally performed according to conventional methods well known in the art and as described in various references that are cited and discussed throughout the present specification. See e.g., Sambrook et al., Molecular Cloning: A Laboratory Manual (3rd ed., Cold Spring Harbor Laboratory Press, Cold Spring Harbor, N.Y. (2001)), which is incorporated herein by reference.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Described herein is a technique whereby one can orient a recombinant protein (polypeptide) on a surface for subsequent use or to provide a favored site for the chemical addition of fluorescent, biotin, or similar molecules. To achieve this goal, a charged peptide is genetically appended to either the amino or carboxyl terminus of the polypeptide. Charged residues in the charged peptide will be both electrostatically attracted to an oppositely charged surface and provide the groups involved in the covalent attachment of the protein to the surface, and thereby orient the protein on the surface. These charged residues within the fusion protein would also be highly accessible and reactive for addition of a dye or biotin molecule, thereby avoiding interfering with the active site on the protein when chemically labeling the recombinant protein. As described below, this technique was particularly effective with single-domain antibodies.

Single-domain antibodies (sdAbs) are recombinant derivatives of heavy-chain-only antibodies found in camelids and sharks. Heavy-chain-only antibodies are distinct from conventional antibodies in that they lack the typical heavy-chain/light-chain structure. The binding element for conventional antibodies is composed of both a heavy-chain variable domain and light-chain variable domain so that the functional component of the antibody is divided between two distinct proteins. By contrast, the binding element of a heavy-chain-only antibody is composed of a single domain. This confers two features that have been exploited. First, this binding domain can be isolated from the heavy-chain and used as a very small (~15 kDa) functional protein by itself. Secondly, as compared to a conventional antibody, the lack of posttranslational modifications in sdAbs allows for their production in bacterial expression systems rather than more complex and costly eukaryotic systems. The basic structure, composition, preparation, and uses of relevant antibodies are described in, for example, U.S. Pat. Nos. 5,800,988; 5,840,526; 5,874,541; 6,005,079; 6,015,695; and 6,765,087. Use of the term "antibody," "sbAb," or the like herein includes reference to fusion proteins thereof.

Genetic fusions of single domain antibodies (sdAb) with biotin binding proteins facilitated their oriented attachment to biotin surfaces, and provided a more active capture surface for immunoassay applications than sdAb that were covalently attached in a relatively random orientation. While the use of biotin binding protein fusion molecules were effective, the present inventors were interested in finding a method to achieve the same result without the need to attach a large protein to the sdAb. Thus, the utility of a positively charged, lysine-containing peptide appended to the carboxyl terminus of the sdAb was evaluated.

Exemplary Configurations

It was contemplated that the lysines on the C-terminus of the sdAb would enable directional immobilization using standard EDC/NHS chemistry that is a commonly utilized linking chemistry for proteins to surfaces. Structurally, the binding loops of sdAb are located on the opposite side from their C-terminus, resulting in an orientation with the positive, lysine-containing tail coupled to the surface and the binding region oriented for optimal antigen capture. This has potential to dramatically enhance the percentage of active protein immobilized. For the initial attempt to test this hypothesis, a genetic construct termed sdAb clone C8 (which binds ricin) was genetically linked to a positively charged leucine zipper (termed +Zip) having the amino acid sequence AAAGGGGSGGGGSGGGGSAQLKKKLQAL-KKKNAQLKWKLQALKKKLAQGGD (SEQ ID No: 1). The utility of this tail to provide oriented immobilization of an anti-ricin sdAb and the subsequent improvement in the ability of the sensor to detect ricin was demonstrated.

To demonstrate the range of this concept, a smaller positively charged peptide (termed GS-3K), and having the amino acid sequence AAAGGGGSGGGGSKKK (SEQ ID No: 2) was tested and found to not hinder the recombinant production of the sdAb to the same degree as positively charged leucine zipper did. This sdAb-GS-3K construct would also provide an oriented capture surface that was significantly more active than when the sdAb was randomly attached. The sdAb-GS-3K was demonstrated for oriented attachment to MagPlex microspheres first. The concept was repeated using two different sdAb and their corresponding sdAb-GS-3K constructs that were prepared. Tests found the oriented immobilized sdAb-GS-3K to provide enhanced detection of ricin relative to the randomly attached sdAb. These results were later confirmed by SPR measuring the improvement in ricin capture by the oriented sdAb-GS-3K relative to random sdAb using SPR GLC sensor chips, designed by Bio-Rad for general amine coupling via a compact polymer layer.

Figure 1:
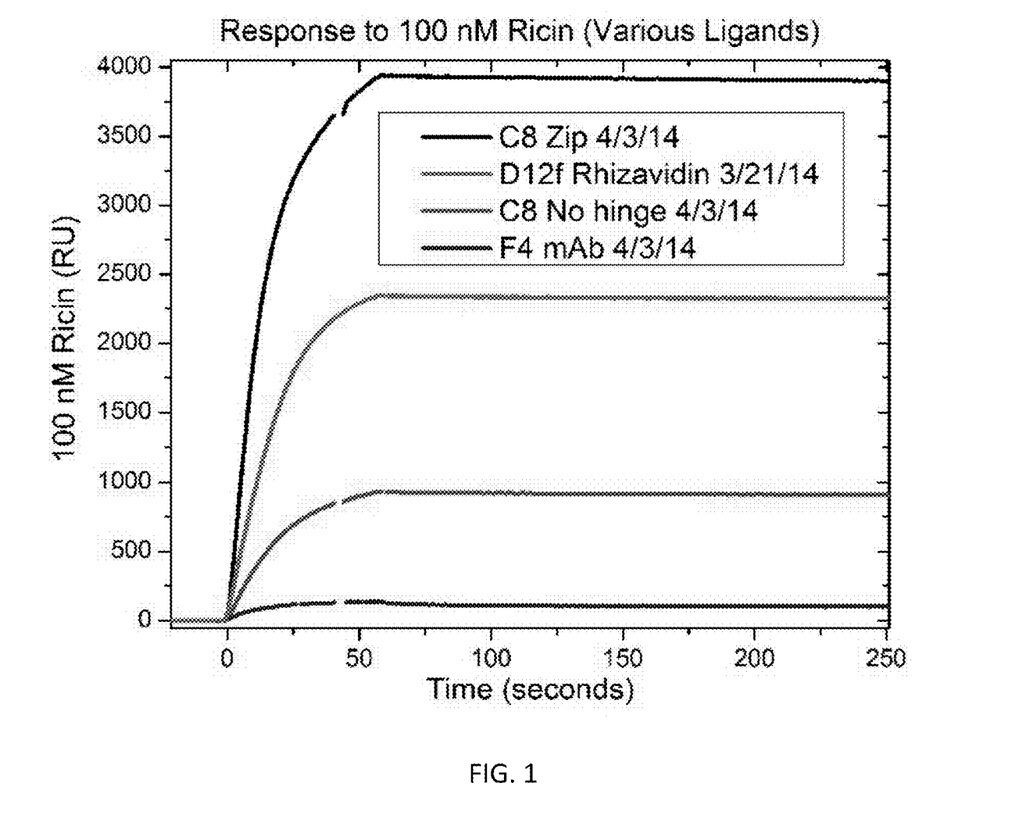
FIG. 1 shows the amount of ricin bound by anti-ricin sdAb or mAb attached to a surface plasmon resonance (SPR) sensor surface. It can be seen that the C8-+Zip was much more active, binding >4-fold more ricin than did C8-sdAb that lacked the positively charged tail. For comparison, results showing a related ricin binding sdAb D12f linked to the biotin binding protein rhizavidin attached to a biotin surface, as well as covalently attached anti-ricin mAb are shown. Neither performed as well as the C8-+Zip. For the data shown, similar amounts of C8-sdAb and C8-+Zip had been covalently attached to the surface, (3,500 and 4,300 RUs respectively).
Figure 2:
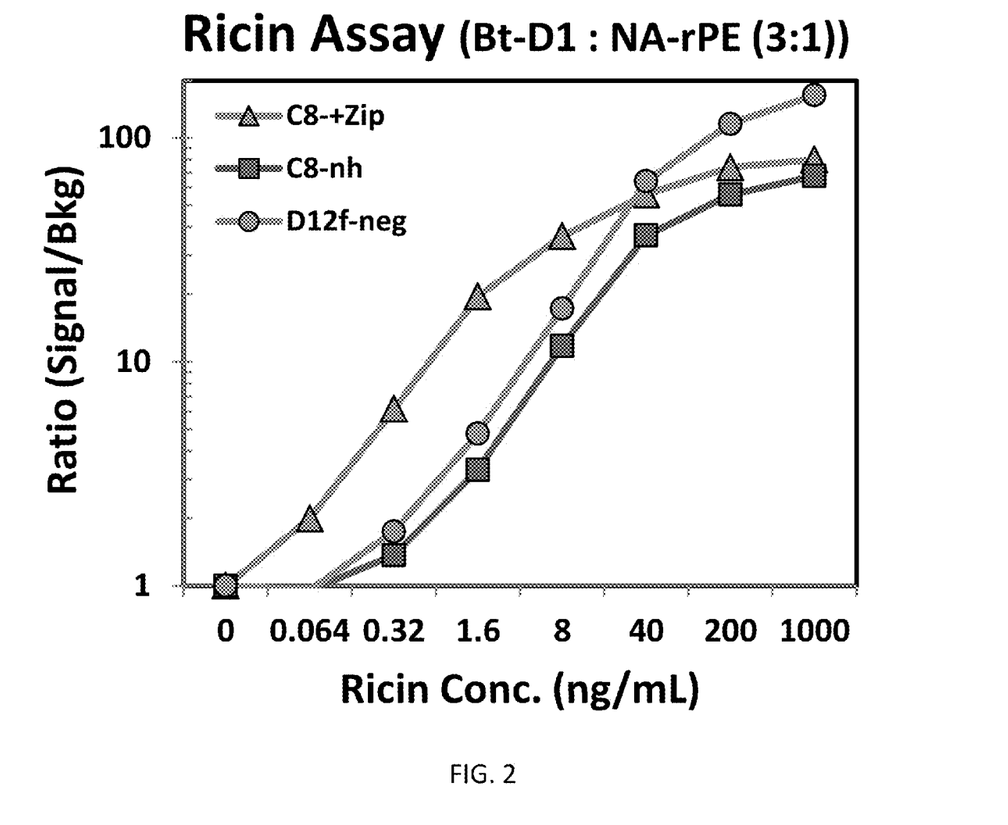
FIG. 2 shows a comparison of oriented C8-+Zip with random C8 and D12f-neg, as capture ligands immobilized on Luminex MagPlex microspheres. For this assay the microspheres were mixed with various amounts of ricin, then the amount bound was evaluated by addition of another anti-ricin sdAb which had been biotinylated followed by the signal generating NeutrAvidin-R-Phycoerythrin.
Figure 3:
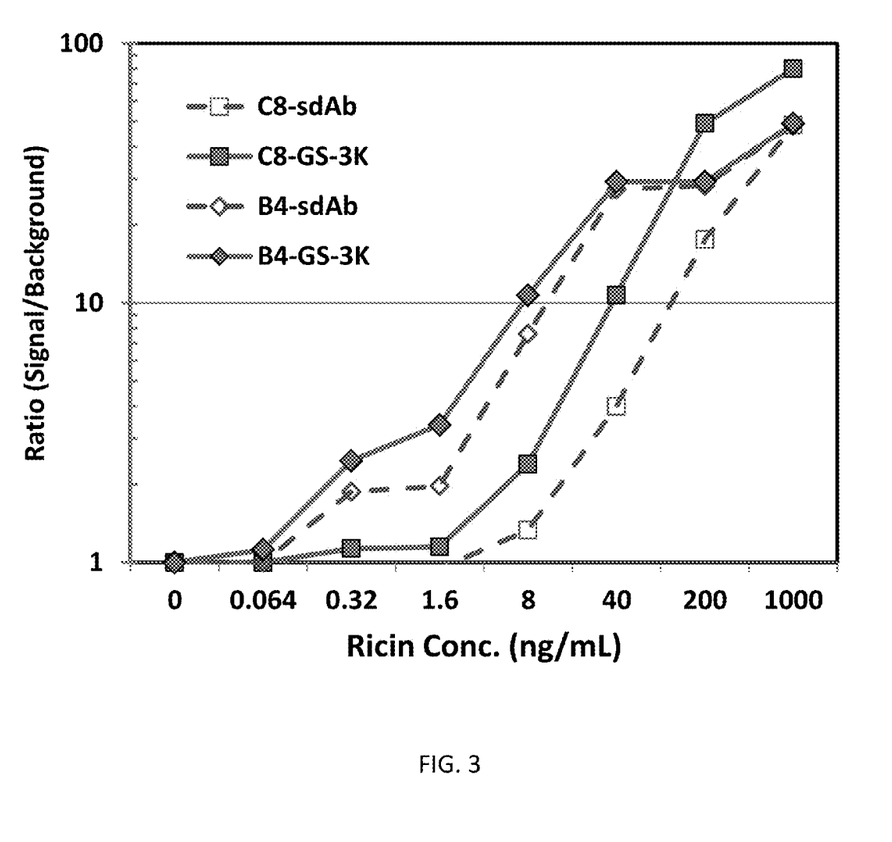
FIG. 3 shows a MagPlex bead based fluorimmunoassay for ricin, showing the improvement realized by using carboxyl microspheres coated with sdAb-GS-3K versus the standard sdAb. Two different anti-ricin sdAb were prepared in both formats and improvement was observed in each case.
Figure 4:
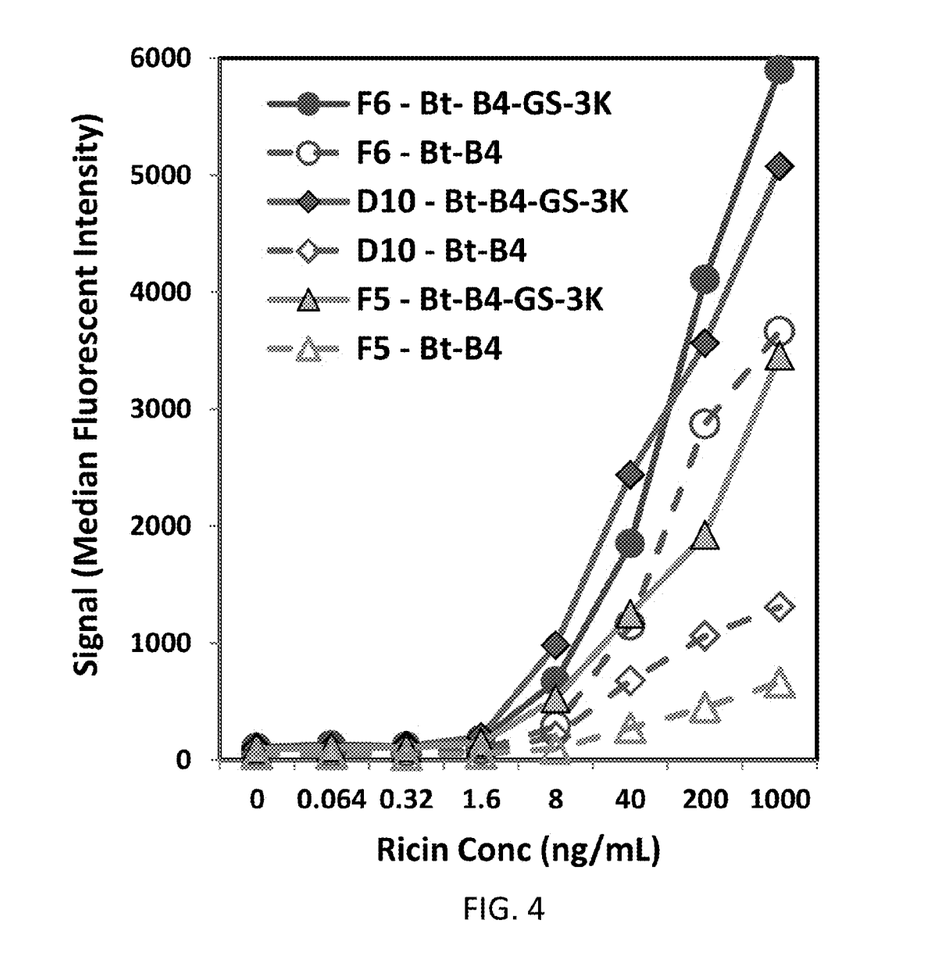
FIG. 4 shows a MagPlex bead based fluorimmunoassay for ricin, showing the improvement realized by using biotinylated detector sdAb that include the GS-3K tail versus those without the tail. Regardless of the capture bead set utilized, the biotinylated B4-GS-3K sdAb was superior to the standard biotinylated B4 sdAb.

To optimize activity of an immobilized recombinant protein, it is preferred that the binding site remains unobstructed and that the molecule retains substantial freedom of movement. Likewise, when one prepares a chemical conjugate of a protein it is ideal to place the added molecule sufficiently far from the protein active/binding site that no impairment in activity occurs. To achieve these results, additional amino acids which included a number of positively charged residues (lysine) were genetically added to the C-terminal end of a ricin binding single domain antibody (sdAb). When this sdAb with the positive tail, which was termed C8-positive-leucine-zipper-his and had the amino acid sequence EVQLQASGGGLVQGGDSLRLSCAASGRTLGDYGVA-WFRQAPGKEREFVSVISRSTIITDYANSVKGRFTISRD-NAKNAVYLQMNSLKPEDTAVYYCAVIANPVYATSR-NSDDYGHWGQGTQVTVSSAAAGGGGSGGGGSGG-GGSAQLKKKLQALKKKNAQLKWKLQALKKKLAQ-GGDALEHHHHHH (SEQ ID No: 3), was utilized in place of the same sdAb that lacked the positive tail, which was termed c8-GS-3k and had the amino acid sequence EVQLQASGGGLVQGGDSLRLSCAASGRTLGDYGVA-WFRQAPGKEREFVSVISRSTIITDYANSVKGRFTISRD-NAKNAVYLQMNSLKPEDTAVYYCAVIANPVYATSR-NSDDYGHWGQGTQVTVSSEPKTPKPQPAASGAEFA-AAGGGGSGGGGSKKKALEHHHHHH (SEQ ID No: 4), the percentage of protein that immobilized in an active orientation onto a negatively charged SPR surface, used as supplied, dramatically increased by >4 fold, as seen in FIG. 1. Thus, enhanced sensitivity for toxin detection is expected. This same strategy is also effective for immobilization onto other carboxyl modified surfaces such as color coded magnetic beads (MagPlex). In this case the difference was not as dramatic, but still between 50 to 100% increase in active capture antibody was realized by addition of the positively charged tail (FIG. 2). Similar improvements were observed when the shorter GS-3K tail was used in place of the +Zip tail (FIG. 3). The positively charged tail was also effective at providing an attachment point for molecules of interest. Biotin is often chemically attached to lysine residues of proteins in a random fashion; however this can result in loss of activity. By providing multiple highly accessible lysines the labeling can be substantially directed towards the positive tail, and thereby improve the resulting activity of the protein. In addition, the increased accessibility of the biotin may improve the subsequent binding the streptavidin-enzyme/fluorophore bioconjugates required to complete the signal transduction. This was demonstrated to provide signal enhancements from 50 to 100%, depending on the sdAb being evaluated (FIG. 4). In a like manner, one should be able to add a fluorophore instead of a biotin and achieve a similar enhancement. Note that, in addition to the above-described charged peptides, these contructs included the sequence ALEHHHHHH (SEQ ID No: 5) to incorporate a restriction enzyme site and poly-histidine tag for purification.

Figure 5:
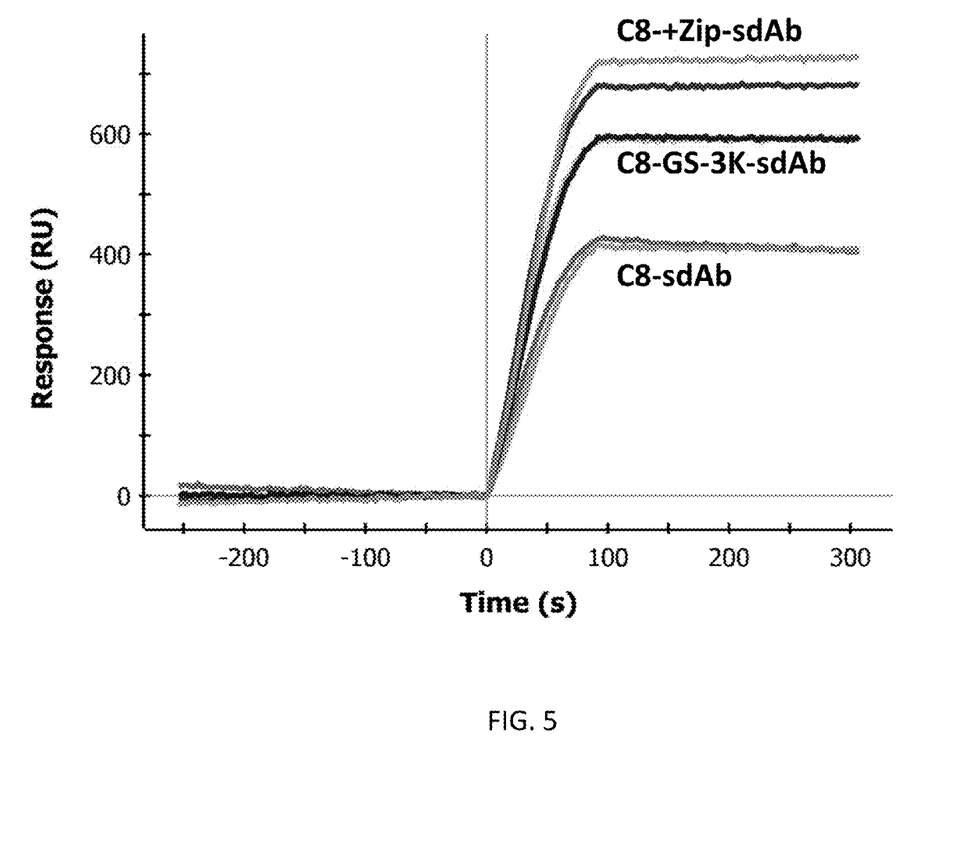
FIG. 5 shows surface plasmon resonance (SPR) results of 33 nM ricin A chain detection of similar amounts of C8 sdAb, C8-GS-3K sdAb, and C8-+Zip sdAb immobilized on an SPR chip. The signal increase was 1.7 fold for the +Zip linker and 1.4 fold for the GS-3K linker.

Another example demonstrated an improvement in ricin detection using an oriented sdAb versus random, in this case showing a signal increase of 1.7 fold for the +Zip linker and 1.4 fold for the GS-3K linker. This illustrates that both linkers consistently resulted in improvement over the standard recombinant protein (FIG. 5).

Figure 6A:
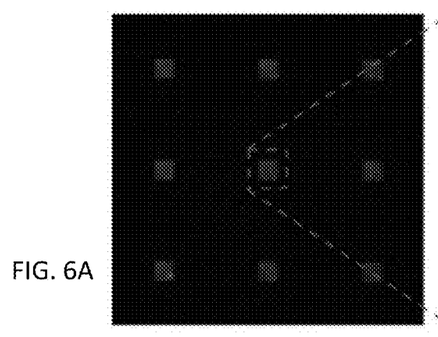
FIG. 6A shows LSPRi of 9 representative arrays, each array consisting of 400 nanostructures.
Figure 6B:
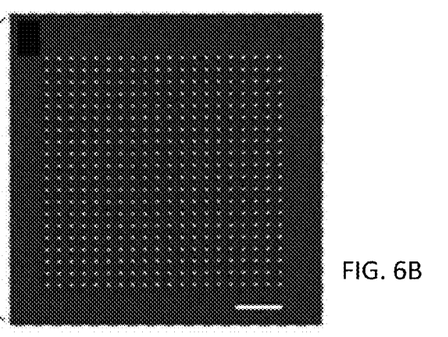
FIG. 6B is a scanning electron micrograph of an array of 400 nanostructures. The original image was false colored red to indicate the resonance wavelength of 635 nm.
Figure 6C:
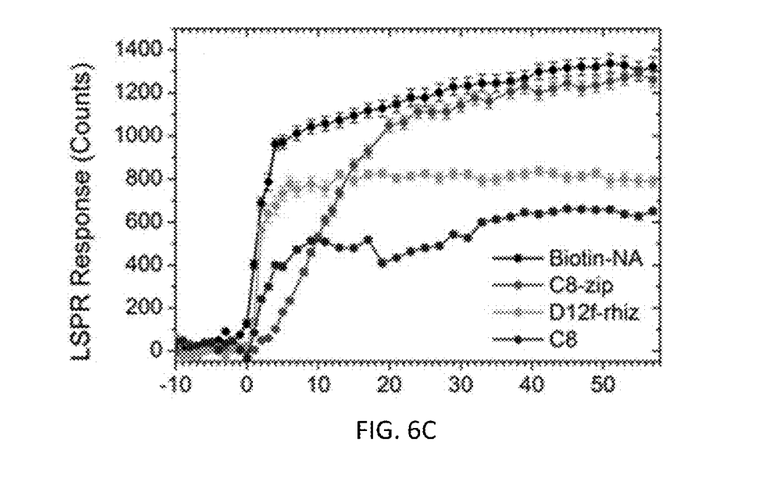
FIG. 6C shows the LSPRi response to 100 nM ricin for C8-zip (C8-+Zip), C8 and D12f-rhiz optimally prepared surfaces.

Another example, illustrated in FIGS. 6A-6C, shows the utility of the sdAb+Zip to orient capture molecules for use on a nanoplasmonic platform with localized surface plasmon resonance spectroscopy (LSPR). This demonstrates the cross platform utility of this methodology.

Following initial binding, covalent attachment can be made using 1-Ethyl-3-(3-dimethylaminopropyl)carbodiimide (EDC) crosslinking chemistry. Other forms of covalent attachment can be made as known in the art.

One key advantage of this methodology is that it makes use of the surface chemistry already being widely utilized, thus it is relatively transparent to the user. Many detection/measurement systems make use of carboxyl modified surfaces for the attachment of biomolecules, the technique described here make use of these same surfaces but achieves on average a much more active and oriented molecule on that surface. This method is highly flexible, in that while it was demonstrated with sdAb, it is expected to operate on nearly any recombinant protein such as single chain antibodies, enzymes, etc. In addition, the utility is not simply for the immobilization to surfaces, but the same tail can be utilized for the addition of molecules such as biotin, fluorophores, dyes, or other molecules of interest. It is further contemplated that the addition of negatively charged leader sequences or tails should could useful for attachment to positively charged (lysine) surfaces.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. A fusion protein consisting of:
   a single-domain antibody; and
   a positively-charged domain with 100% sequence identity to SEQ ID No: 2 fused to a C-terminus of the single-domain antibody.

\* \* \* \* \*